United States Patent
Tucker et al.

(10) Patent No.: US 8,494,624 B2
(45) Date of Patent: Jul. 23, 2013

(54) METHOD AND APPARATUS FOR REDUCING NOISE IN BRAIN SIGNAL MEASUREMENTS

(75) Inventors: Don M. Tucker, Eugene, OR (US); Don M. Tucker, Sr., Eugene, OR (US)

(73) Assignee: Electrical Geodesics, Inc., Eugene, OR (US)

( * ) Notice: Subject to any disclaimer, the term of this patent is extended or adjusted under 35 U.S.C. 154(b) by 414 days.

(21) Appl. No.: 12/803,397

(22) Filed: Jun. 25, 2010

(65) Prior Publication Data
US 2010/0274153 A1    Oct. 28, 2010

(51) Int. Cl.
*A61B 5/04* (2006.01)

(52) U.S. Cl.
USPC .......................... 600/544; 600/407; 702/191

(58) Field of Classification Search
USPC ............................ 600/544, 545, 407; 702/191
See application file for complete search history.

(56) References Cited

U.S. PATENT DOCUMENTS

| | | | |
|---|---|---|---|
| 7,286,871 B2 | 10/2007 | Cohen | |
| 2004/0249302 A1* | 12/2004 | Donoghue et al. | 600/544 |
| 2005/0268916 A1* | 12/2005 | Mumford et al. | 128/207.13 |
| 2006/0120571 A1* | 6/2006 | Tu et al. | 382/118 |
| 2009/0287107 A1* | 11/2009 | Beck-Nielsen et al. | 600/544 |

OTHER PUBLICATIONS

Srinivasan et al. "Estimating the spatial Nyquist of the human EEG", Behavior Research Methods, Instruments, & Computers, 1998, 30 (1), 8-19.*

Freeman et al., "Spatial spectra of scalp EEG and EMG from awake humans," Clinical Neurophysiology 114 (2003) pp. 1053-1068.

* cited by examiner

*Primary Examiner* — Navin Natnithithadha
*Assistant Examiner* — Etsub Berhanu
(74) *Attorney, Agent, or Firm* — Portland Intellectual Property, LLC

(57) ABSTRACT

A method and apparatus for reducing noise in brain signal measurements. The method provides an array of sensors providing for spatial oversampling, and multiple samplings over time to produce measurement data. The measurement data have a variance common to the sensors, and a remaining variance that can be safely assumed to be sensor or channel specific noise and that is accounted for by a suitable modification of the measurement data. The apparatus provides clusters of the sensors positioned in correspondence to the vertices of substantially equilateral triangles that are defined by tensile elements connecting the clusters.

6 Claims, 3 Drawing Sheets

US 8,494,624 B2

METHOD AND APPARATUS FOR REDUCING NOISE IN BRAIN SIGNAL MEASUREMENTS

FIELD OF THE INVENTION

The present invention relates to methods and apparatus for reducing noise in brain signal measurements.

BACKGROUND

EEG and MEG are common techniques for measuring, at the surface of the head, electric and magnetic field potentials generated by operation of the brain. An array of sensors, typically electrodes in the case of EEG, and SQUID sensors in the case of MEG, is provided, the sensors being distributed over the head surface.

There is an understanding in the art regarding the number of sensors needed to accurately record the electrical or magnetic field potentials produced by brain activity, and 64 sensors is recognized as being insufficient. The understanding derives from the Nyquist theorem, which is often used to define the minimum temporal sampling rate for sampling a continuous signal based on the highest frequency (Fourier) component of the signal. According to the Nyquist theorem, to fully code and therefore fully define a continuous signal having a highest frequency component of frequency X, the signal must be sampled at a sampling rate of 2X. In practice, the signal is sampled at a higher rate, typically about 2.5 X, to account for the non-stepwise response of real filters, i.e., real filters "roll off" over a frequency range.

The Nyquist theorem has been extended in the present art to define spatial frequencies, i.e. the number of cycles of a signal, or a Fourier component thereof, per unit distance (e.g., X is expressed in cycles/cm). Thus, there is a theoretical minimum Nyquist sampling rate (theoretical maximum spacing between sensors) of $½·X^{-1}$, where $X^{-1}$ is the spatial period.

As in the time domain, there is a corresponding practical minimum spacing of about $1/(2.5)·X^{-1}$, corresponding to a higher sensor density. The difference is $0.10·X^{-1}$ or 25%, and is referred to as "spatial oversampling." Spatial oversampling, like time oversampling, is provided for the purpose of complying with the Nyquist theorem in practice, to ensure that the signal is in fact fully and faithfully characterized by the data.

Spatial oversampling has been used in academic research, such as exemplified by Walter J. Freeman et al. ("Spatial spectra of scalp EEG and EMG from awake humans," Elsevier Clinical Neurophysiology 114 (2003) 1053-1068). But spatial oversampling is typically not utilized in commercial practice, as it leads to higher cost and complete accuracy has not been considered essential.

SUMMARY

Disclosed is a method specifically for reducing noise in brain signal measurements, but which may be utilized for reducing noise in an electrical or magnetic signal produced by any organ in the body. The signal will have a highest spatial frequency component of X cycles per unit measure of distance. The method includes steps of (a) providing, on or outside the exterior surface of the body, an array of sensors, each of the sensors for independently measuring the signal, wherein the sensors are spaced apart from one another by at least a minimum spacing of $½·X^{-1}$; (b) sampling the signal, by each sensor, at a plurality of different times, so as to produce, for each sensor, a set of time-dependent measurements of the signal; (c) identifying a first variance in the measurements corresponding to a selected sensor that is common to the measurements corresponding to all of the other sensors; (d) identifying a remaining variance in the measurements corresponding to the selected sensor; and (e) removing from the measurements corresponding to the selected sensor a second variance that is determined, at least in part, by the remaining variance, so as to reduce or eliminate noise that is unique to the measurements of the selected sensor.

Also disclosed is an apparatus for reducing or eliminating noise in an electrical or magnetic signal produced by an organ in the body. The apparatus includes an array of first sensors, each first sensor for independently measuring the signal, wherein, within a first predetermined set of three of the first sensors, the first sensors thereof are connected to each other by three separate tensile connecting elements defining a substantially equilateral "geodesic" triangle, with the first sensors of the first predetermined set corresponding to vertices of the geodesic triangle. The apparatus further includes an array of second sensors, each second sensor for independently measuring the signal, wherein a predetermined second set of the second sensors is associated with a respective one of the sensors of the first set, defining a cluster of first and second sensors, the sensors of the cluster being connected to each other by a common structure, wherein the second sensors of the cluster are all closer to the first sensor of the cluster than to either of the remaining sensors of the first set.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DETAILED DESCRIPTION OF PREFERRED EMBODIMENTS

Figure 1:
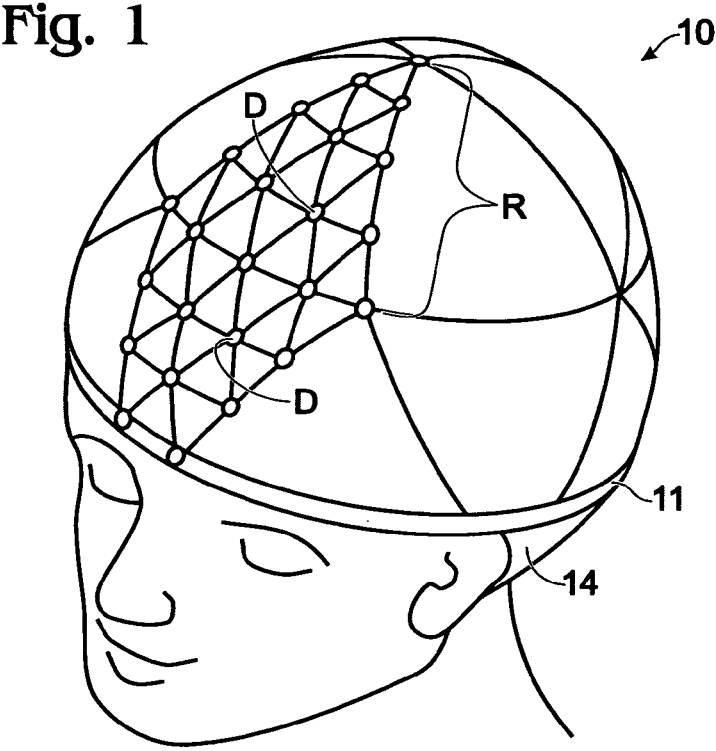
FIG. 1 is a reproduction of FIG. 1 of U.S. Pat. No. 5,291,888.

FIG. 1 shows the inventor's "geodesic sensor net" (10) which was the subject of U.S. Pat. No. 5,291,888, which is incorporated by reference herein in its entirety. As explained in the '888 Patent, the net provides for positioning an array of EEG electrodes or other sensors on the surface of the head 14, for measuring electrical or magnetic energy that is perceived as a "signal," and which is reduced to digital data referred to as field data. In general, the sensors may or may not be positioned so as to make contact with the head surface.

Each sensor responds to the signal at its particular location. The signal is produced primarily by the operation of the brain, and it is therefore of interest to characterize that activity, particularly to locate the actual sources of the activity. This requires solving what is well known in the art as "the inverse problem," which hypothesizes sources of electrical or magnetic activity in the brain and adjusts either or both their locations and their characteristics to fit the field data recorded at the sensors.

It was noted above that spatial oversampling is typically not utilized in commercial practice, as it leads to higher cost and complete accuracy has not been considered essential. A reason for this may be that solving the inverse problem is inherently inexact.

The signal evolves over time, and the sensors sense the time-varying activity of multiple sources as a single spatially varying signal.

The invention is based on a recognition that spatial oversampling can be used to reduce or eliminate noise in the signal. Typical signal noise includes ambient noise, such as from fluorescent lighting, local electromyographic ("EMG") noise due to the activity of muscles proximate the sensors, and channel noise, which is electrical noise in the circuit between the signal being measured and the ultimate output. Each sensor has its own associated channel, comprising the sensor, an amplifier, an analog-to-digital converter, and cabling for connecting the sensor to a computer for analysis; and all of these components are noise sources that produce noise unique to each channel. It has been determined that EMG noise is highly local and therefore also substantially unique to each channel.

To reduce or eliminate channel specific signal noise, the present invention requires at least some degree of spatial oversampling. Preferably, to ensure that the signal is fully and faithfully captured by the sensors as a practical matter, the amount of spatial oversampling is at least 25%; it is more preferably at least 50%; it is more preferably still at least 75%; and it is most preferably at least 100%, However, hereinafter, "spatial oversampling" is defined as being sampling at any rate higher than the theoretical minimum.

The signal is oversampled in space; however, the signal is also sampled in time. To illustrate, assume there are N sensing sensors, each typically producing a voltage output, but the output could be any output, or "measurement." At "m" different times t=1, t=2, . . . t=m, the outputs of each of the N sensing sensors is sampled. Thus, each particular sensing sensor $N_P$ provides a set of measurements [$N_P$ (t=1), $N_P$ (t=2), . . . $N_P$ (t=m)]. These data define samples (in time) of the variable $N_P$, and the samples will exhibit a variance.

It is an important recognition of the present inventor that, if the signal is spatially oversampled, variance in a particular time dependent variable $N_P$ due to brain signal will be shared by all the variables N, whereas variance that is unique to the variable $N_P$ can properly be identified as channel specific noise and subtracted out of the measurement.

Figure 2:
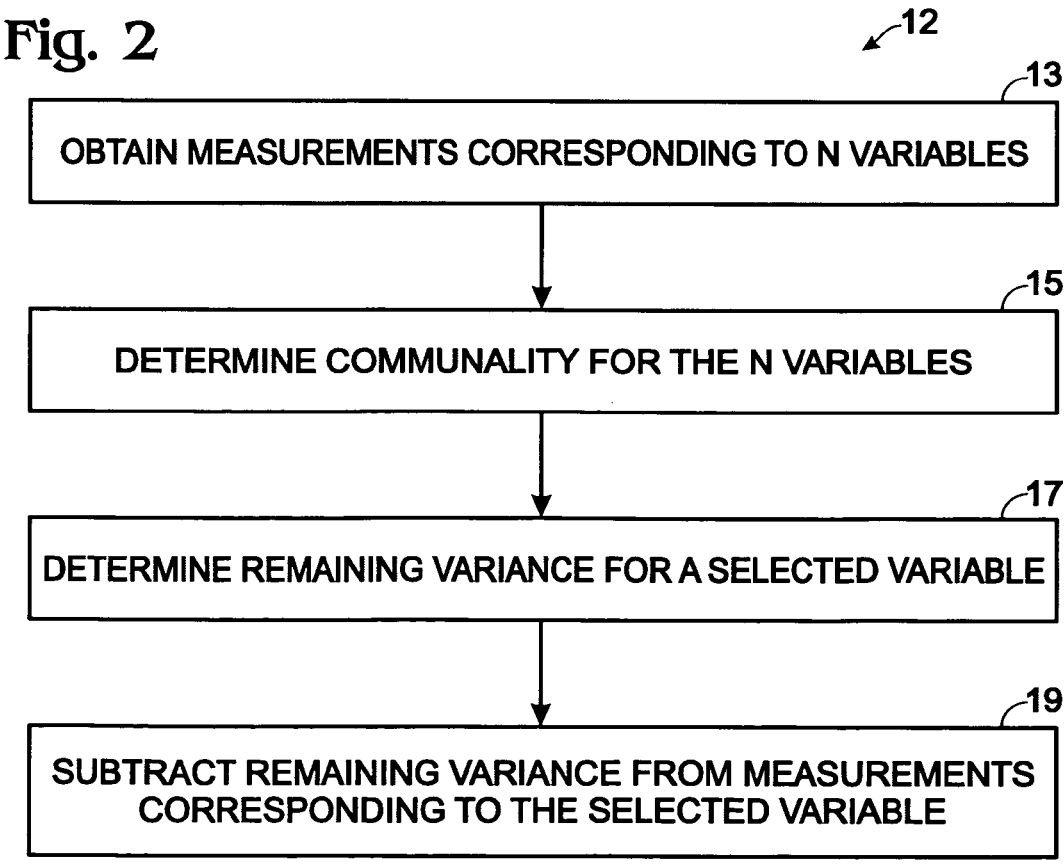
FIG. 2 is a flow chart of a method for reducing noise in brain signal measurements according to the present invention.

Then, referring to FIG. 2, with respect to a particular variable $N_P$ residing within a set of variables N, the following steps may be performed according to a preferred method 12 according to the invention: (13) obtain measurements corresponding to N variables; (15) determine a "communality," i.e., a variance that is common to all the variables N; (17) utilize the result of step (15) to determine a remaining variance for a selected variable $N_P$, where this variance is assumed to be unique to the variable $N_P$; and (19) subtract the result in step (17) from the measurements of the variable $N_P$, to assure at least a reduction in the amount of sensor/channel unique noise.

Communality can be determined and understood by reference to "principal factors analysis," which is used in statistics to classify the variables in a set of variables. Essentially, the method is as follows: Each variable is correlated with each other variable, typically by a regression analysis. The correlations are "best fit" lines (or other functions) that relate two variables. For example, the line y=mx+b relates two variables x and y. The regression line (or other function) defines a derived variable that can substitute for the original pair of variables. For example, the derived variable z=mx−y+b can substitute for an original pair of variables (x, y) that are related as y=mx+b. This derived variable is referred to as a "factor."

The regression analysis is specifically to find the line (or other function) that (a) maximizes the variation of the derived variable while (b) minimizing the variance around the derived variable. The variation (a) is "predicted" by the regression line (or other function), and therefore represents a variance that has been "extracted" by the factor, whereas the variation (b) is not predicted by the regression line (or other function).

In general, there are N variables and each factor reduces the dimensionality of the variable space by one; thus factoring can be carried out N−1 successive times, to define the variance that can be accounted for by factoring, which is the "communality." For each variable, any remaining variance can be safely assumed to be variable specific under the assumption of spatial oversampling.

There may be methodologies other than principal factors analysis for estimating or determining an amount of variation in a variable that is common to other variables in a set of variables, and/or an amount of variation that is not common to other variables in the set, and it should be understood that the particular methodology used is not critical to the invention.

Preferably, spatial oversampling according to the invention makes use of principles articulated in the aforementioned '888 Patent, which will be briefly reviewed herein.

The '888 Patent describes a "sensor net" 10, as shown in FIG. 1. The net 10 is generally affixed to the subject's head by use of a headband 11.

Figure 3:
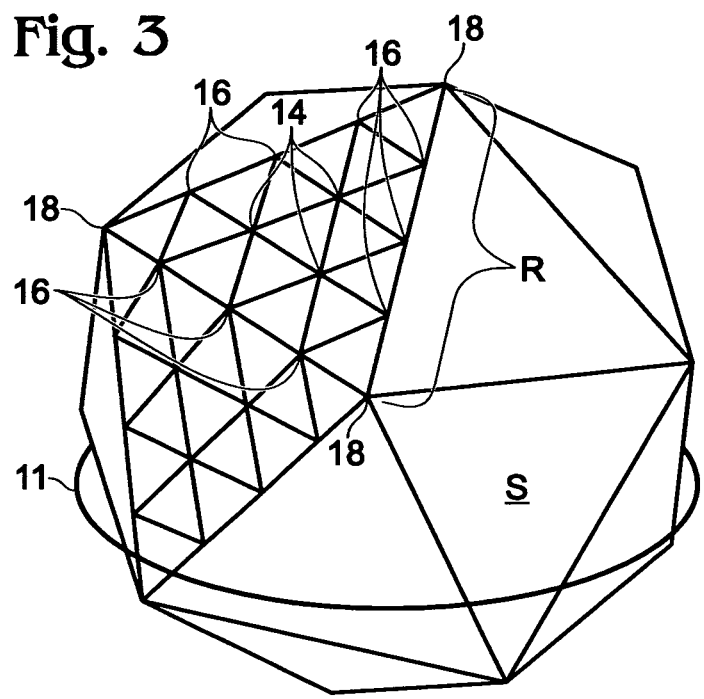
FIG. 3 is an isometric view of an icosahedron, subdivided into geodesic triangles according to the teachings of the '888 Patent.

A partitioning principle employed for the net is shown in FIG. 3, by which the head is modeled as an icosahedron. A reference marker "R" is indicated in FIG. 10 which corresponds to the portion of the net 10 indicated with same marker in FIG. 1.

Referring to FIG. 3, each of the 20 sides "S" of the icosahedron is an equilateral triangle, referred to as a "basic" triangle in the '888 Patent, and each of these is partitioned into sixteen smaller equilateral triangles, referred to as "geodesic" triangles in the '888 Patent. This partitioning defines three internal vertices 14; nine edge vertices 16 that are each shared between two adjacent sides; and three corner vertices 18 that are each shared between five sides. Accordingly, there are 3+9/2+3/5 vertices associated with a given side.

The corresponding geodesic structure of the net 10 in FIG. 1 is defined by elastic tensile members connected between "pedestals" (not shown) at the vertices. The pedestals mount sensors "D" at, preferably, each of the vertices.

Similar partitioning of each geodesic triangle into sixteen yet smaller equilateral triangles is currently not practical, but would be a preferred distribution scheme for providing additional sensors for oversampling.

Figure 4:
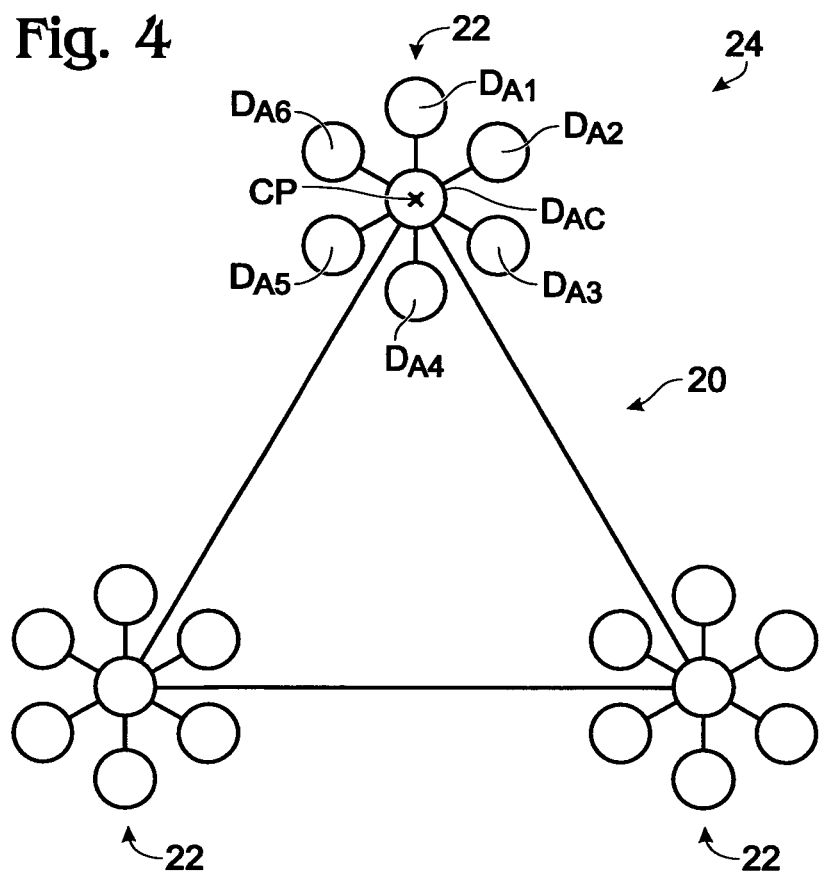
FIG. 4 is a plan view of a portion of a net 24 according to the present invention for distributing sensors used for sensing and/or stimulating brain activity.

As a practical alternative, in a net 24 according to the present invention, each sensor D as shown in FIG. 1 is replaced with a cluster or "pod" 22 having the hexagonal configuration shown in FIG. 4. Particularly, FIG. 4 shows a single geodesic triangle 20 of the net 24, having three vertices at each of which, instead of a single sensor D, there is a pod 22 defining an assembly of seven sensors $D_A$. In the pod shown in FIG. 11, there is a central sensor $D_{AC}$ which is disposed at a center-point "CP" of the pod. The center-point CP is preferably disposed at one of the vertices of the geodesic triangle 20, so that the sensor $D_{AC}$ occupies the position of the original sensor. The sensor $D_{AC}$ may be omitted, however. In any case, there are six satellite sensors $D_{A1-A6}$, hexagonally distributed around the center-point CP. Preferably, in each pod 22 there are one or more relatively rigid elements, compared to the elastic tensile members, connecting the sensors $D_{A1-A6}$ and the central sensor $D_{AC}$. The one or more relatively rigid elements together define a "common structure." The rigidity of the common structure provides the advantage of maintaining a substantially fixed spacing between the sensors of a cluster.

It will be noted that the spacing between each central element $D_{AC}$ is greater than the spacing between the central element and its associated satellite elements $D_{A1-A6}$. It should also be noted that oversampling does not in general require consistent spacing between samples.

A hexagonal distribution of six satellite sensors $D_{A1-A6}$ for a given central sensor such as shown in FIG. 4 is preferred, this being recognized by the present inventor to reinforce, by reflection, the original geodesic structure. The arrangement may be recognized as a fractal. However, the satellite sensors may be distributed other than uniformly or symmetrically, they may be at different distances from the central sensor, and there may be more or fewer than six in number, without departing from the principles of the invention.

For example, there may be: five satellite sensors, preferably but not necessarily distributed so as to define the vertices of a pentagon; four satellite sensors, preferably but not necessarily distributed so as to define the vertices of a square or rectangle; or seven or more satellite sensors, likewise preferably, though not necessarily, distributed uniformly or symmetrically about, and therefore at the same distance from, the central sensor. A "semi-fractal" arrangement, which would be somewhat preferred if a sufficient number of sensors could be obtained to provide the necessary oversampling, would employ three satellite sensors distributed so as to define the vertices of an equilateral triangle.

The net 24 provides a sensor density increased by sevenfold over the net 10. Typically, the net 10 included 256 sensors, and therefore the net 24 preferably has 1792 sensors, providing an additional 1536 sensors and a corresponding six-fold increase in sensor density (1536/256=6).

Figure 5:
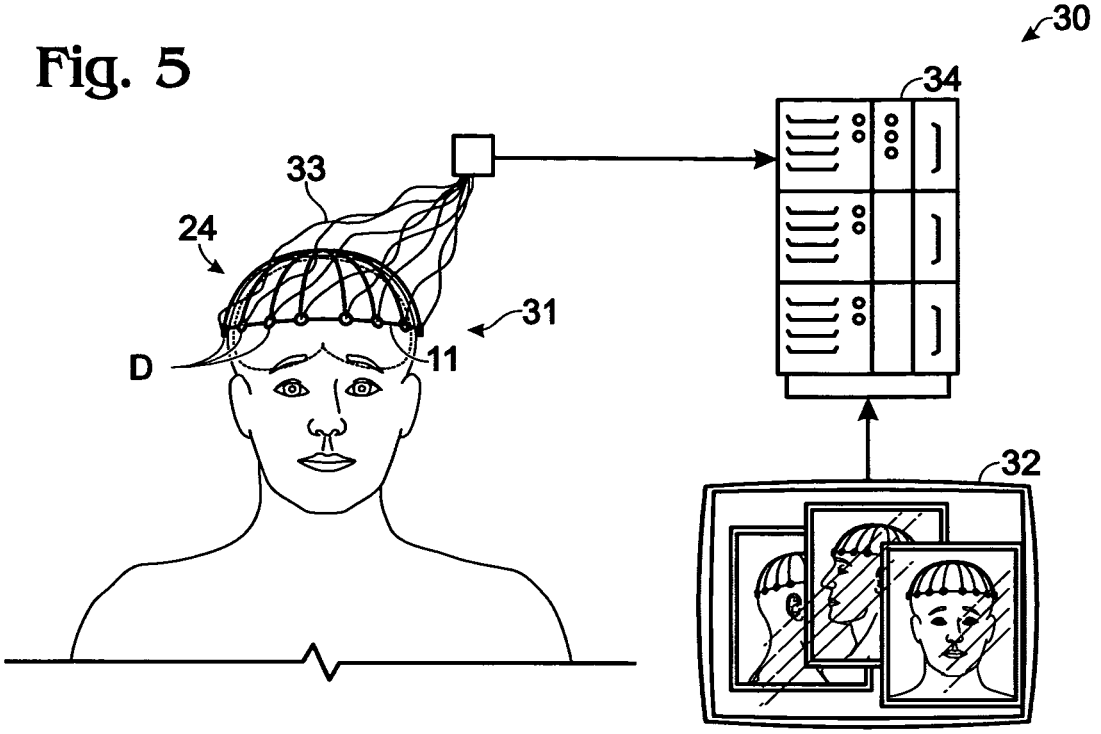
FIG. 5 is a block diagram of a system for reducing noise in brain signal measurements according to the invention, utilizing the method of FIG. 2 and the sensor net of FIG. 4.

FIG. 5 shows a preferred system 30 for reducing noise in brain signal measurements according to the principles described above. The system 30 includes the sensor net 24, which is fitted around the subject's head 31 in the same manner as the net 10 is shown in FIG. 1.

The sensors D of the net 24 are typically electrodes that make intimate contact with the skin. It is generally important to know the location of the sensors on the head, and there are known means for accomplishing this. A preferred methodology utilizing a photogrammetric system (referenced as 32 in FIG. 5) is described in U.S. Pat. No. 7,190,826.

The sensors D are connected through respective channels 33 as described above to a computer 34 that receives, digitizes, and processes data provided by the sensors to produce measurement data as described above. According to the invention, the measurement data are further processed so as to determine a communality as described above in connection with step 15, a remaining variance as described above in connection with step 17, and a subtraction as described above in connection with step 19. The computer 34 therefore produces measurement data that have been corrected for error due to sensor/channel specific noise.

The computer 34 is also provided the sensor location information from the system 32. Utilizing the measurement data and the location information, the computer is adapted to solve the inverse problem as known in the art.

It will be readily appreciated that the computational duties described above may be shared between any number of computers, which may be linked together or not.

It is to be understood that, while a specific method and apparatus for reducing noise in brain signal measurements has been shown and described as preferred, other configurations and methods could be utilized, in addition to those already mentioned, without departing from the principles of the invention. It should also be understood that, while the disclosed methods and apparatus are particularly adapted for use in measuring brain signals, the same principles can be applied for measuring bioelectrical or biomagnetic signals associated with other organs in the body, such as the heart.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for reducing or eliminating noise in an electrical or magnetic signal produced by an organ in the body, the signal having a highest spatial frequency component of X cycles per unit measure of distance, the method comprising:
   providing, on or outside the exterior surface of the body, an array of sensors, each of said sensors for independently measuring the signal, wherein the sensors are spaced apart from one another by at least a minimum spacing of $\frac{1}{2} \cdot X^{-1}$;
   sampling the signal, by each sensor, at a plurality of different times, so as to produce, for each sensor, a set of time-dependent measurements of the signal;
   identifying a first variance in the measurements corresponding to a selected sensor that is common to the measurements corresponding to all of the other sensors;
   identifying a remaining variance in the measurements corresponding to the selected sensor; and
   removing from the measurements corresponding to the selected sensor a second variance that is determined, at least in part, by said remaining variance, so as to reduce or eliminate noise that is unique to the measurements of the selected sensor.

2. The method of claim 1, wherein said step of providing includes providing at least 256 sensors in said array.

3. The method of claim 2, the method further comprising disposing said sensors on the head of the body, to measure a brain signal.

4. The method of claim 3, the method further comprising solving an inverse problem of source localization after performing said step of removing.

5. The method of claim 4, further comprising specifying said second variance to be substantially equal to said remaining variance.

6. The method of claim 1, further comprising specifying said second variance to be substantially equal to said remaining variance.

* * * * *